(12) United States Patent
Xue et al.

(10) Patent No.: US 11,845,980 B2
(45) Date of Patent: *Dec. 19, 2023

(54) EMULSION COMPOSITIONS AND METHODS OF THEIR USE

(71) Applicant: Bio-Rad Laboratories, Inc., Hercules, CA (US)

(72) Inventors: Yi Xue, Shrewsbury, MA (US); Joshua Ritchey, Melrose, MA (US); Robert Meltzer, Belmont, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/665,170

(22) Filed: Feb. 4, 2022

(65) Prior Publication Data

US 2022/0154266 A1    May 19, 2022

Related U.S. Application Data

(63) Continuation of application No. 16/921,453, filed on Jul. 6, 2020, now Pat. No. 11,274,337, which is a continuation of application No. 15/882,098, filed on Jan. 29, 2018, now Pat. No. 11,118,217.

(60) Provisional application No. 62/452,330, filed on Jan. 30, 2017.

(51) Int. Cl.
| | | |
|---|---|---|
| *C12Q 1/68* | (2018.01) | |
| *C12Q 1/6848* | (2018.01) | |
| *C12Q 1/686* | (2018.01) | |
| *C12Q 1/6844* | (2018.01) | |
| *C12Q 1/6816* | (2018.01) | |

(52) U.S. Cl.
CPC ........... *C12Q 1/6848* (2013.01); *C12Q 1/686* (2013.01); *C12Q 1/6846* (2013.01); *C12Q 1/6816* (2013.01); *C12Q 2527/125* (2013.01); *C12Q 2563/159* (2013.01)

(58) Field of Classification Search
CPC .... C12Q 1/6848; C12Q 1/6846; C12Q 1/686; C12Q 1/6816; C12Q 2527/125; C12Q 2563/159
See application file for complete search history.

(56) References Cited

U.S. PATENT DOCUMENTS

| | | |
|---|---|---|
| 6,793,938 B2 | 9/2004 | Sankaram |
| 10,676,778 B2 | 6/2020 | Lowe et al. |
| 2011/0027394 A1 | 2/2011 | McClements et al. |
| 2011/0217712 A1 | 9/2011 | Hiddessen et al. |
| 2011/0256592 A1 | 10/2011 | Beckers et al. |
| 2013/0109575 A1 | 5/2013 | Kleinschmidt et al. |
| 2014/0170736 A1 | 6/2014 | Heredia et al. |
| 2014/0302503 A1 | 10/2014 | Lowe et al. |
| 2017/0022538 A1 | 1/2017 | Abate et al. |

FOREIGN PATENT DOCUMENTS

| | | |
|---|---|---|
| CN | 102317472 A | 1/2012 |
| CN | 104861088 A | 8/2015 |
| CN | 105189785 A | 12/2015 |

OTHER PUBLICATIONS

International Search Report and Written Opinion from PCT/US2018/015687 dated May 17, 2018; 14 pages.
Jeong B. et al.; "Thermosensitive sol-gel reversible hydrogels"; Advanced Drug Delivery Reviews; vol. 64; 2012; pp. 154-162.
Li, J. et al.; "Formation of Supramolecular Hydrogels Induced by Inclusion complexation between Pluronics and alpha-Cyclodextrin"; Macromolecules; vol. 34; 2001; pp. 7236-7237.
Li, J. et al.; "Block-Selected Molecular Recognition and Formation of Polypseudorotaxanes between Poly(propylene oxide)-Poly(ethylene oxide)-Poly(propylene oxide) Triblock Copolymers and alpha-Cyclodextrin"; Angew. Chem. Int. Ed.; vol. 42, No. 1; 2003; pp. 69-72.
Li, J. et al.; "Preparation fna Characterization of Polypseudorotaxanes Based on Block-Selected Inclusion Complexation between Poly(propylene oxide)-Poly(ethylene oxide)-Poly(propylene oxide) Triblock Copolymers and alpha-Cyclodextrin"; J. Am. Chem. Soc.; vol. 125; 2003; pp. 1788-1795.
Li, J. et al.; "Cyclodextrin-based supramolecular architectures: Syntheses, structures, and applications for drug and gene delivery"; Advanced Drug Delivery Reviews; vol. 60; 2008; pp. 1000-1017.
Pradal, C. et al.; "Gelation Kinetics and Viscoelastic Properties of Pluronic and alpha-Cyclodextrin-Based Pseudopolyrotaxane Hydrogels"; Biomacromolecules; vol. 14; 2013; pp. 3780-3792.
Tan, L. et al.; "Stimuli-induced gel-sol transition of multi-sensitive supramolecular beta-cyclodextrin grafted alginate/ferrocene modified pluronic hydrogel"; Soft Matter; vol. 8; May 2012; pp. 5746-5749.
Van de Manakker, F., et al. "Self-Assembling Hydrogels Based on Beta-Cyclodextrin/Cholesterol Inclusion Complexes"; Macromolecules; vol. 41; 2008; pp. 1766-1773.
Zhang et al.; "Dual-Functional PEI-Poly(Gamma-Cholesterol-L-Glutamate) Copolymer for Drug/Gene Co-delivery"; Macromolecular Chemistry and Physics; vol. 215, Issue 2; Jan. 2014; pp. 163-170.
Extended European Search Report in EP Appln. 18744615.8 dated Jun. 29, 2020; 8 pages.
Dominski, A. et al.; "[alpha]-Cyclodextrin-Based Polypseudorotaxane Hydrogels"; Materials; vol. 13, No. 1; Dec. 28, 2019; p. 133; 28 pages.
Huang, et al.; "Supramolecular Hydrogels Based on Cyclodextrin Poly(Pseudo)Rotaxane for New and Emerging Biomedical Applications"; *Advanced Healthcare Materials*; 2014; pp. 405-438.
Liu, K. et al.; "Supramolecular hydrogels based on cyclodextrin-polymer polypseudorotaxanes: materials design and hydrogel properties"; *Soft Matter*; vol. 7; 2011; pp. 11290-11297.

*Primary Examiner* — Jezia Riley
(74) *Attorney, Agent, or Firm* — Kilpatrick Townsend and Stockton LLP

(57) ABSTRACT

Emulsion compositions are provided herein. Also provided herein are kits containing one or more emulsion compositions or components for making such emulsion compositions. Also provided herein are methods of using such emulsion compositions, such as for amplification of target nucleic acids in emulsion droplets.

19 Claims, 6 Drawing Sheets

EMULSION COMPOSITIONS AND METHODS OF THEIR USE

CROSS-REFERENCE TO RELATED PATENT APPLICATIONS

The present application is a continuation of U.S. patent application Ser. No. 16/921,453, filed Jul. 6, 2020, which a continuation of U.S. patent application Ser. No. 15/882,098, filed Jan. 29, 2018, now U.S. Pat. No. 11,118,217, which claims benefit of priority to U.S. Provisional Patent Application No. 62/452,330, filed Jan. 30, 2017, each of which is incorporated by reference for all purposes.

BACKGROUND OF THE INVENTION

Microfluidic processes often employ the use of an emulsion, which contains droplets (herein referred to as "emulsion droplets") of a dispersed liquid phase surrounded by an immiscible continuous liquid phase. Emulsion droplets may be used as reaction vessels for chemical or biological reactions, as storage vessels, and/or as a method to isolate and compartmentalize molecules, such as chemical or biological elements. A population of emulsion droplets (herein referred to interchangeably as a "population" or "library") may be composed of droplets of many different sizes (polydispersed population) or droplets of relatively same size (monodispersed population). With proper chemistry including polymers, amphiphilic compounds, surfactants, and the like on the surface of the emulsion, droplets may be made "stable," meaning they are substantially prevented from mixing and merging when in contact with each other. This stability allows one to create a population or library of droplets composed of different chemical or biological components that may be stored in the approximately same volume of space without mixing or contamination between and/or among the components of one droplet and another. This property of stabilized emulsion droplets is useful for many applications in performing chemical and biological reactions, storage and compartmentalization.

One approach for stabilization of emulsion droplets is to include a cross-linkable agent (e.g., a cross-linkable protein) in the emulsion. After droplet generation, the cross-linkable agent can be treated to initiate cross-linking, thereby forming a solid "skin" at the droplet interface. See, for example, U.S. 2011/0027394 and U.S. 2011/0217712. However, these cross-linkable agents can increase the propensity of surface fouling or clogging in microfluidic droplet handling devices, and can inhibit droplet merging and/or injection techniques.

BRIEF SUMMARY OF THE INVENTION

Described herein are stable water-in-oil emulsion droplet compositions, and methods and compositions for forming and using stable emulsion droplets, including but not limited to microfluidic methods for analyzing biological analytes. The stable water-in-oil emulsion droplet compositions typically include an aqueous phase that comprises a cyclodextrin and a polymer, wherein at least a portion of the cyclodextrin and polymer in the aqueous phase form a host-guest complex. Without wishing to be bound by theory, it is believed that in some embodiments the stabilization is due to formation by the host-guest complexes of a thermally reversible hydrogel. The thermally reversible hydrogel can be gelate (gel) phase at high temperature and a solution (sol) phase at low temperature. For example, the hydrogel can be gel at a PCR annealing temperature such as 50° C., a PCR extension temperature such as 72° C., a PCR denaturation temperature such as 95° C., or a combination two or more thereof. Additionally or alternatively, the hydrogel can be sol at, e.g., room temperature or below. In some embodiments, at least a portion of the host-guest complexes formed in the aqueous phase of the water-in-oil form a rotaxane, a pseudorotaxane, a polyrotaxane, or a polypseudorotaxane.

In one aspect, the present invention provides an emulsion comprising a water-in-oil emulsion droplet, the droplet comprising: water; a plurality of cyclodextrin molecules; and a plurality of polymer molecules, wherein individual polymer molecules of the plurality comprise a hydrophobic moiety and/or a hydrophilic moiety, wherein the aqueous phase of the droplet comprises a thermally reversible hydrogel, and wherein the droplet is present in a continuous oil phase. In some cases, the thermally reversible hydrogel is hydrogel at a temperature above a gel sol transition temperature and liquid at a temperature below the gel sol transition temperature. In some embodiments, the thermally reversible hydrogel is in a gel form at a temperature of at least about 60° C. or 70° C. and no more than about 98° C. and a sol form at temperature of less than about 50° C. or 30° C. and greater than about 0° C.

In one aspect, the present invention provides an emulsion comprising a water-in-oil emulsion droplet, the droplet comprising: water; a plurality of cyclodextrin molecules; and a plurality of polymer molecules, wherein individual polymer molecules of the plurality comprise a hydrophobic moiety and/or a hydrophilic moiety, wherein at least a portion of the cyclodextrin molecules and the polymer molecules form a plurality of polypseudorotaxane complexes, and wherein the droplet is present in a continuous oil phase.

In one aspect, the present invention provides an emulsion comprising a water-in-oil emulsion droplet, the droplet comprising: water; a plurality of cyclodextrin molecules; and a plurality of amphiphilic polymer molecules, wherein individual amphiphilic polymer molecules of the plurality comprise a hydrophobic moiety and a hydrophilic moiety, wherein at least a portion of the cyclodextrin molecules and the amphiphilic polymer molecules form a plurality of polypseudorotaxane complexes, and wherein the droplet is present in a continuous oil phase.

In some embodiments, individual cyclodextrin molecules of the plurality are independently selected from the group consisting of an α-cyclodextrin, and a β-cyclodextrin. In some embodiments, individual cyclodextrin molecules of the plurality are independently selected from the group consisting of an α-cyclodextrin, and a γ-cyclodextrin. In some embodiments, individual cyclodextrin molecules of the plurality are independently selected from the group consisting of a β-cyclodextrin, and a γ-cyclodextrin. In some embodiments, at least a portion of individual cyclodextrin molecules of the plurality independently comprise a hydrophobic modification.

In some embodiments, individual cyclodextrin molecules of the plurality are independently a compound of Formula I:

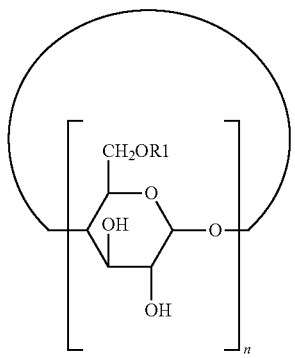

wherein: each R1 is independently selected from the group consisting of a hydrophobic group, a sulfite, and H, where the hydrophobic group is selected from alkyl, alkenyl, alkynyl, haloalkyl, cycloalkyl, aryl, and any combination thereof, and the sulfite is a $(C_1\text{-}C_6\text{-alkyl or alkylene})\text{-}SO_3^-$ group; and n is 6, 7, or 8.

In some embodiments, the emulsion comprises a mixture of at least two structurally different cyclodextrin molecules. In some embodiments, the at least two structurally different cyclodextrin molecules are independently a compound of Formula I, wherein n is 6. In some embodiments, the at least two structurally different cyclodextrin molecules are independently a compound of Formula I, wherein n is 7. In some embodiments, the at least two structurally different cyclodextrin molecules are independently a compound of Formula I, wherein n is 8.

In some embodiments, each R1 is independently H or an hydroxyalkyl, wherein at least one R1 is hydroxyalkyl. In some embodiments, each R1 is independently H or a $C_2\text{-}C_6$ hydroxyalkyl, wherein at least one R1 is $C_2\text{-}C_6$ hydroxyalkyl. In some embodiments, each R1 is independently H or a $C_2\text{-}C_6$ hydroxyalkyl, wherein at least one R1 is 2-hydroxypropyl. In some embodiments, R1 is 2-hydroxypropyl. In some embodiments, the cyclodextrin molecules are 2-hydroxypropyl α-cyclodextrin.

In some embodiments, the amphiphilic polymer molecules comprise block co-polymers, wherein the block co-polymers comprise a hydrophilic block and a hydrophobic block. In some embodiments, the block co-polymers are di-block co-polymers or tri-block co-polymers, or a combination thereof. In some embodiments, the block co-polymers are di-block co-polymers comprising a polyethylene glycol (PEG) hydrophilic block and a hydrophobic block.

In some embodiments, the block co-polymers are di-block co-polymers comprising a hydrophilic block and a hydrophobic block comprising polypropylene glycol. In some embodiments, the block co-polymers are di-block co-polymers comprising a hydrophilic block and a hydrophobic block comprising a cholesterol or a derivative thereof. In some embodiments, the block co-polymers are tri-block co-polymers. In some embodiments the tri-block co-polymers are poloxamers. In some embodiments, the poloxamers are poloxamer 188.

In some embodiments, the amphiphilic polymer molecules are non-ionic amphiphilic polymer molecules. In some embodiments, the amphiphilic polymer molecules are linear amphiphilic polymer molecules. In some embodiments, the amphiphilic polymer molecules have a weight average molecular weight of from about 2,000 g/mol to about 70,000 g/mol.

In some embodiments, the droplet comprises a mass ratio of cyclodextrin molecules to amphiphilic polymer molecules of from about 1:4 to about 4:1. In some embodiments, the droplet comprises a mass ratio of cyclodextrin molecules to amphiphilic polymer molecules of about 1:1. In some embodiments, the droplet comprises a concentration of cyclodextrin molecules of from about 0.5% to about 4% mass per volume (m/v). In some embodiments the concentration of cyclodextrin molecules is about 2% m/v. In some embodiments, the droplet comprises a concentration of amphiphilic polymer molecules of from about 0.5% to about 4% mass per volume (m/v). In some embodiments, the concentration of amphiphilic polymer molecules is about 2% m/v. In some embodiments the cyclodextrin molecules are at a concentration of about 2% and the amphiphilic polymer molecules are at a concentration of about 2%.

In some embodiments, the droplet further comprises a thermostable DNA-dependent DNA polymerase or an RNA-dependent DNA polymerase. In some embodiments, the droplet further comprises nucleic acid. In some embodiments, the droplet further comprises a thermostable DNA-dependent DNA polymerase or an RNA-dependent DNA polymerase. In some embodiments, the droplet further comprises: a nucleic acid; and a thermostable DNA-dependent DNA polymerase or an RNA-dependent DNA polymerase, wherein the DNA polymerase is heterologous to the nucleic acid.

In some embodiments, the droplet comprises nucleotide triphosphates (NTPs), deoxyribonucleotide triphosphates (dNTPs), or the combination thereof. In some embodiments, the droplet comprises a thermally reversible hydrogel. In some embodiments, the thermally reversible hydrogel is in a gel form at a temperature of between about 70° C. and about 98° C. and a sol form at temperature of less than about 50° C. and greater than about 0° C. In some embodiments, the thermally reversible hydrogel is in a gel form at a temperature of between about 60° C. and about 98° C. and a sol form at temperature of less than about 30° C. and greater than about 0° C.

In some embodiments, the droplet is present in a continuous fluorocarbon oil phase. In some embodiments, the continuous fluorocarbon oil phase comprises a fluorous oil and a surfactant. In some embodiments, the surfactant is a fluorosurfactant. In some embodiments, the fluorosurfactant is a block co-polymer comprising a perfluorinated polyether block and a polyethylene glycol block. In some embodiments, the fluorosurfactant comprises a poly(perfluoro propyleneoxide) jeffamine tri-block copolymer, a poly(perfluoro propyleneoxide) amide tri-block copolymer, a poly(perfluoro propyleneoxide) PEG di-block copolymer, or a poly(perfluoro propyleneoxide) PEG tri-block copolymer.

In some embodiments, the fluorous oil comprises methyl nonafluorobutyl ether (HFE-7100), ethyl nonafluorobutyl ether (HFE-7200), 2-trifluoromethyl-3-ethoxydodeca-fluorohexane (HFE-7500), 1,1,1,2,2,3,4,5,5,5-decafluoro-3-methoxy-4-trifluoromethyl-pentane (HFE-7300), Perfluorooctylbromide, Perfluorodecalin, FC-40, FC-43, FC-70, FC-84, FC-72, RM-82, FC-75, RM-101, or a combination thereof. In some embodiments, the fluorous oil is HFE-7500. In some embodiments, the droplet is present in a continuous silicone oil phase. In some embodiments, the continuous silicone oil phase comprises a silicone oil and a surfactant.

In some embodiments, the droplet forms a contact angle of at least about 90° with a cyclic olefin polymer surface after incubating the droplet for at least about 1 hr at a temperature of about 95° C. In some embodiments, the droplet forms a contact angle of about 115° with a cyclic olefin polymer surface after incubating the droplet for at least about 1 hr at a temperature of about 95° C. In some embodiments, the emulsion comprises at least 100, or at least 1,000 water-in-oil emulsion droplets.

In another aspect, the present invention provides a method of forming an emulsion according to any one of the foregoing aspects or embodiments, the method comprising: combining a continuous oil phase, an aqueous solution, a plurality of cyclodextrin molecules, and a plurality of amphiphilic polymer molecules, under conditions wherein at least a portion of the cyclodextrin molecules and the amphiphilic polymer molecules form a plurality of polypseudorotaxane complexes, thereby forming an emulsion comprising a water-in-oil emulsion droplet. In some embodiments, the aqueous solution is a buffered aqueous solution.

In another aspect, the present invention provides a method of using an emulsion comprising a water-in-oil emulsion droplet, the method comprising: providing the emulsion according to any one of the foregoing emulsion aspects or embodiments; heating the droplet to a temperature of between about 50° C. to about 100° C.; cooling the droplet to a temperature below about 50° C.; and optionally repeating the heating and cooling between 1-50 times. In some embodiments, after the cooling or the optionally repeated heating and cooling, the method further comprises injecting at least a portion of the droplet interior into a second droplet. In some embodiments, the droplet comprises a target nucleic acid or an amplicon or reverse transcription product thereof. In some embodiments, the second droplet comprises a detection reagent for detecting the presence or absence of the target nucleic acid or the amplicon or reverse transcription product thereof.

In some embodiments, after the cooling or the optionally repeated heating and cooling, the method further comprises injecting at least a portion of the droplet interior into a plurality of second droplets. In some embodiments, the droplet comprises a target nucleic acid or an amplicon or reverse transcription product thereof. In some embodiments, the plurality of second droplets comprise detection reagents for detecting the presence or absence of the target nucleic acid or the amplicon or reverse transcription product thereof. In some embodiments, the detection reagents are different in different second droplets injected with a portion of the first droplet, wherein the different detection reagents detect a presence or absence of a different target nucleic acid or of a different amplicon or reverse transcription product thereof.

In some embodiments, the emulsion comprises at least 100 or at least 1,000 water-in-oil emulsion droplets, and the method comprises: providing the emulsion comprising the at least 100 or at least 1,000 water-in-oil emulsion droplets; heating the droplets to a temperature of between about 50° C. to about 100° C.; cooling the droplets to a temperature below about 50° C.; and optionally repeating the heating and cooling between 1-50 times. In some embodiments, after the cooling or the optionally repeated heating and cooling, the method further comprises injecting at least a portion of the droplet interiors into a plurality of second droplets.

DETAILED DESCRIPTION OF THE INVENTION

I. Introduction

Figure 1:
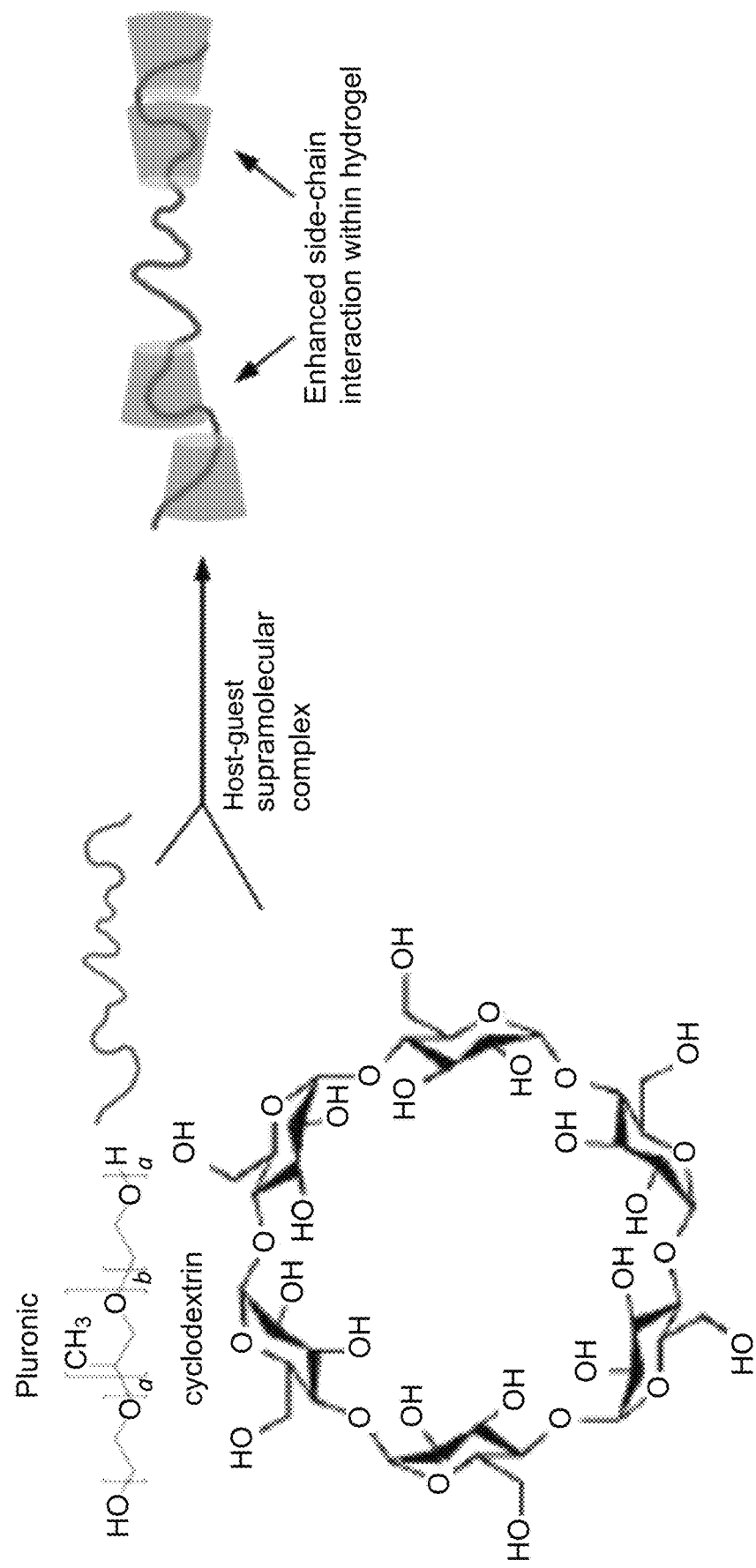
FIG. 1 illustrates an exemplary host-guest complex between a cyclodextrin and a polymer that can be used to stabilize a water-in-oil emulsion droplet described herein.

The inventors have discovered compositions that provide stable water-in-oil emulsion droplets. These stable water-in-oil emulsions comprise droplets in which the aqueous phase contains a cyclodextrin and a polymer capable of forming a host-guest complex with the cyclodextrin. The cyclodextrin and polymer in the droplets can form a thermally reversible hydrogel in the aqueous phase, at the water-oil interface, or both. The sol-gel transition temperature of the thermally reversible hydrogel can be adjusted by altering the cyclodextrin, the cyclodextrin concentration, the polymer, the polymer concentration, or a combination thereof. In some cases, the stability provided by the cyclodextrin and polymer in the aqueous phase is further enhanced with a compatible oil phase composition.

II. Compositions

Compositions provided herein comprise aqueous mixtures of cyclodextrin and polymer. In some embodiments, the aqueous mixtures provide a thermally-reversible hydrogel. In some embodiments, the compositions comprise water-in-oil (W/O) emulsion droplets that include the aqueous mixture (e.g., include an aqueous mixture that forms a thermally-reversible hydrogel). In some cases, the thermally reversible hydrogel is in a gel form at a temperature of between about 30° C. and about 99° C., or more. In some cases, the thermally reversible hydrogel is in a gel form at a temperature of between about 40° C. and about 99° C., about 40° C. and about 95° C. or 98° C., about 45° C. and about 99° C., about 45° C. and about 95° C. or 98° C., about 50° C. and about 99° C., about 50° C. and about 95° C. or 98° C., about 60° C. and about 99° C., about 60° C. and about 95° C. or 98° C., about 70° C. and about 99° C., about 70° C. and about 98° C., or about 70° C. and about 95° C.

In some cases, the thermally reversible hydrogel is in a sol form at temperature of less than about 70° C. and greater than about 0° C., or less. In some cases, the thermally reversible hydrogel is in a sol form at a temperature of between about 60° C. and about 4° C., about 50° C. and about 4° C., about 45° C. and about 4° C., about 40° C. and about 4° C., about 35° C. and about 4° C., about 30° C. and about 4° C., about 25° C. and about 4° C., about 25° C. and about 10° C., about 25° C. and about 15° C., or about 35° C., about 30° C., about 25° C., or about 20° C.

As noted above, the aqueous mixture (e.g., thermally reversible hydrogel forming aqueous mixture) can comprise a cyclodextrin and a polymer capable of forming a host-guest complex with the cyclodextrin. In some embodiments, the cyclodextrin and polymer are at a cyclodextrin:polymer mass ratio of from about 0.1:1 to about 10:1, from about 0.2:1 to about 5:1, from about 1:4 to about 4:1, from about 0.3:1 to about 3:1, from about 0.5:1 to about 2:1, or about 1:1. In some embodiments, the cyclodextrin and polymer are at a cyclodextrin:polymer molar ratio of from about 100:1 to about 1:1, from about 50:1 to about 2:1, from about 25:1 to about 3:1, from about 15:1 to about 4:1, from about 10:1 to about 5:1, or about 7:1. In some embodiments, the cyclodextrin and polymer are at a cyclodextrin:polymer molar ratio of from about 50:1 to about 1:1, from about 40:1 to about 2:1, from about 30:1 to about 3:1, or from about 20:1 to about 4:1. In some embodiments, the cyclodextrin and polymer are at a cyclodextrin:polymer molar ratio of about 5:1, 6:1, 7:1, 8:1, 9:1 or 10:1.

In some embodiments, the aqueous mixture (e.g., aqueous phase of a W/O emulsion droplet) contains cyclodextrin at a concentration of from about 0.1% to about 10% mass per volume (m/v), from about 0.2% to about 8% m/v, from about 0.3% to about 5% m/v, from about 0.5% to about 4% m/v, from about 1% to about 3% m/v, or about 2% m/v. In some cases, the aqueous mixture (e.g., aqueous phase of a W/O emulsion droplet) contains cyclodextrin at a concentration of about 0.5%, 1%, 2%, 3%, 4%, 5%, 6%, 7%, 8%, 9%, or 10% m/v. In some cases, the aqueous mixture (e.g., aqueous phase of a W/O emulsion droplet) contains cyclodextrin at a concentration of 2% m/v.

In some embodiments, the aqueous mixture (e.g., aqueous phase of a W/O emulsion droplet) contains polymer (e.g., amphiphilic polymer, co-polymer, amphiphilic co-polymer, or homopolymer, as described further below) at a concentration of from about 0.1% to about 10% mass per volume (m/v), from about 0.2% to about 8% m/v, from about 0.3% to about 5% m/v, from about 0.5% to about 4% m/v, from about 1% to about 3% m/v, or about 2% m/v. In some cases, the aqueous mixture (e.g., aqueous phase of a W/O emulsion droplet) contains polymer at a concentration of about 0.5%, 1%, 2%, 3%, 4%, 5%, 6%, 7%, 8%, 9%, or 10% m/v. In some cases, the aqueous mixture contains polymer at a concentration of 2% m/v.

Droplets as described herein can be formed in a water-in-oil emulsion (W/O). The W/O emulsion droplets, or aqueous phase of the W/O emulsion droplets, can be optimized to reduce or eliminate microfluidic surface fouling by selection of appropriate parameters for the cyclodextrin and polymer components. In some embodiments, the aqueous phase of the W/O emulsion droplets is selected to reduce or eliminate surface fouling by minimizing or minimizing a heat-induced change in water droplet contact angle of a microfluidic surface.

In an exemplary embodiment a hydrophobic cyclic olefin polymer (COP) surface is provided, in which a pure water droplet having a volume of approximately 1 µL is placed on the surface. A clean and un-fouled hydrophobic COP surface can be expected to exhibit a contact angle of, of about, of at least, or of at least about 90°, 95°, 100°, 110°, or 115° as measured by a goniometer. The contact angle is generally determined at or near room temperature. Having established that the COP surface is hydrophobic and un-fouled, the water can be removed from the COP surface and then contacted with a test composition under various conditions to determine whether the composition is resistant to COP-surface fouling.

For example, the COP surface can then be contacted with one or more, or all, components of a W/O emulsion droplet composition. In some cases, e.g., an aqueous phase of a W/O emulsion droplet as described herein is contacted with the COP surface for a suitable period of time (e.g., 10 min, 30 min, 1 hr, 3 hr, or longer, or from 10-30 min, or 10-45 min), and at a suitable temperature (e.g., at least 37° C., 40° C., 50° C., 65° C., 75° C., and/or no more than 100° C.). Typically, the temperature is selected to approximate polymerase chain reaction (PCR) denaturation temperature (e.g., 90° C., 95° C., or 98° C.). After testing against the emulsion droplet composition component(s), the COP surface can be cleaned and dried and tested against a 1 µL droplet of pure water as described above to determine whether surface fouling has occurred. As above, the contact angle is generally determined at or near room temperature. Moreover, the conditions (e.g., temperature, humidity, pressure, etc.) for the initial water droplet and the final water droplet are typically chosen to be the same or substantially identical. A change (e.g., reduction) in the contact angle of, of about, of less than, or of less than about 15%, 10%, 5%, or 1%, as compared to the initial pure water droplet, indicates a lack of surface fouling. Generally, the smaller the change, the lower the degree of surface fouling. Conversely a change of greater than 15%, 20%, 25%, 30%, 35%, 40%, or 45% can indicate surface fouling. Generally, the greater the change, the higher the degree of surface fouling.

Additionally or alternatively, an initial control test with a pure water droplet before testing the emulsion composition/components can be unnecessary when the properties of the clean COP surface are well-characterized. Thus, a water droplet contact angle of, of about, of at least, or of at least about 90°, 95°, 100°, 110°, or 115° after contacting with the aqueous phase as described above can indicate a lack of surface fouling. Conversely, a water droplet contact angle of less than about 90°, 80°, 70°, 60°, or 50° can indicate surface fouling. Generally the lower the contact angle, the greater the surface fouling.

In some embodiments, the W/O emulsion droplets are substantially uniform in shape and/or size. For example, in some embodiments, the droplets are substantially uniform in average diameter. For example, in some embodiments, at least 50%, 60%, 70%, 75%, 80%, 85%, 90%, or 95% of the droplets in the population are within 5% of the average droplet size (diameter) of the population. In some embodiments, the droplets have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, about 50 nL, or about 100 nL.

In some embodiments, the number of droplets in the W/O emulsion is, or is at least about 100; 1,000; 5,000; 10,000; 25,000; 50,000; 100,000; $1 \times 10^6$; or $1 \times 10^7$. In some embodiments, the number of droplets is from about 100 to about $1 \times 10^7$, from about 1,000 to about $1 \times 10^7$, from about 1,000 to about $1 \times 10^6$, from about 10,000 to about $1 \times 10^7$, from about 10,000 to about $1 \times 10^6$, from about 10,000 to about $1 \times 10^5$, from about 20,000 to about $1 \times 10^6$, or from about 20,000 to about $1 \times 10^5$.

The droplets can contain one or more biological analytes. Biological analytes can include without limitation, cells (e.g., single cell organisms or cells from a multicellular organism), viruses, proteins, nucleic acids (e.g., RNA or DNA, or the combination thereof), and the like.

The droplets can contain reagents for detection of biological analytes, including but not limited to a protein such as a fluorescent protein and/or an antibody or an enzyme such as a polymerase, peroxidase, luciferase, and/or phosphatase. In some cases, the droplets contain one or more reagents for nucleic acid detection and/or amplification (e.g., thermostable DNA or RNA dependent DNA polymerase, or the combination thereof, dNTPs, buffer, salt, divalent cation, fluorescent dye, fluorescent dye-labeled nucleic acid, etc.). In some cases, a plurality of droplets described herein contain a plurality of different fluorescent dyes, or fluorescent dye concentrations, or a combination thereof. The use of different fluorescent dyes and/or concentrations of fluorescent dyes can provide for highly multiplex analysis.

A. Cyclodextrins

Water-in-oil (W/O) emulsion droplets described herein can contain a cyclodextrin (e.g., a single chemical species of cyclodextrin molecules, albeit in numerous copies) or a mixture of different cyclodextrins. Cyclodextrins are a class of naturally occurring cyclic oligosaccharides containing six (α-cyclodextrin), seven (β-cyclodextrin), or eight (γ-cyclodextrin) D-glucopyranose units. Described herein are various suitable cyclodextrin compositions for providing a stable W/O emulsion droplet. Moreover, it is understood that, in some cases, different cyclodextrin compositions or mixtures thereof can be substituted to further optimize W/O emulsion droplet stability.

As described above, W/O emulsion droplets described herein can contain a mixture of different cyclodextrins. The mixture of different cyclodextrins in an aqueous phase of a W/O emulsion droplet can be in the form of a randomly modified cyclodextrin (e.g., randomly methylated, randomly methacrylated, or randomly hydroxypropylated), or a mixture of randomly modified cyclodextrins. Alternatively, the mixture of different cyclodextrins can be in the form of a mixture of chemically defined modified (i.e., non-randomly modified) or unmodified cyclodextrins, or a mixture of chemically defined modified and unmodified cyclodextrins. As yet another alternative, the mixture of different cyclodextrins can be in the form of a mixture of one or more randomly modified cyclodextrins in combination with one or more chemically defined modified or unmodified cyclodextrins. As used herein, unless otherwise indicated, references to a modified cyclodextrin or a specific species of modified cyclodextrin (e.g., hydroxypropyl (3-cyclodextrin) refers to a fully modified cyclodextrin.

In some embodiments, the W/O droplets contain two or more different cyclodextrins. In some cases, the W/O droplets contain, or contain at least, 3, 4, 5, 6, 7, 8, 9, 10, 11, 12, 13, 14, 15, 16, 17, 18, 19, 20, 21, 22, 23, 24, 25, 26, 27, 28, 29, or 30 different cyclodextrins. In some cases, the W/O droplets contain from 1 to 2, from 1 to 5, from 1 to 10, from 1 to 20, from 1 to 30, from 2 to 5, from 2 to 10, from 2 to 20, from 2 to 30, from 5 to 10, from 5 to 20, from 5 to 30, from 10 to 20, or from 10 to 30 different cyclodextrins.

The cyclodextrin or mixture thereof, can be or contain a modified (e.g., randomly or non-randomly modified) or unmodified α-cyclodextrin, β-cyclodextrin, or γ-cyclodextrin, or a mixture thereof. The cyclodextrin or mixture thereof, can be or contain a modified (e.g., randomly or non-randomly modified) or unmodified α-cyclodextrin, β-cyclodextrin, or a mixture of modified (e.g., randomly or non-randomly modified) or unmodified α-cyclodextrin and β-cyclodextrin. The cyclodextrin or mixture thereof, can be or contain a modified (e.g., randomly or non-randomly modified) or unmodified α-cyclodextrin, γ-cyclodextrin, or a mixture of modified (e.g., randomly or non-randomly modified) or unmodified α-cyclodextrin and γ-cyclodextrin. The cyclodextrin or mixture thereof, can be or contain a modified (e.g., randomly or non-randomly modified) or unmodified β-cyclodextrin, γ-cyclodextrin, or a mixture of modified (e.g., randomly or non-randomly modified) or unmodified β-cyclodextrin and γ-cyclodextrin.

Modified cyclodextrins include cyclodextrins containing one or more hydrophobic modifications. Such hydrophobic modifications include, but are not limited to methyl, ethyl, propyl, isopropyl, hydroxypropyl, butyl, $C_1$-$C_6$ or $C_2$-$C_6$ alkyl or alkylene, $C_1$-$C_6$ or $C_2$-$C_6$ hydroxyalkyl, $C_1$-$C_6$ or $C_2$-$C_6$ hydroxyalkyl acrylate, or $C_1$-$C_6$ or $C_2$-$C_6$ hydroxyalkyl methacrylate. Additionally or alternatively, the modified cyclodextrins can contain one or more hydrophilic modifications such as $C_1$-$C_6$-alkyl or alkylene or $C_2$-$C_6$ alkyl or alkylene)-$SO_3^-$.

In some embodiments, the cyclodextrin or mixture of cyclodextrins is a compound of Formula I or a mixture of compounds of Formula I:

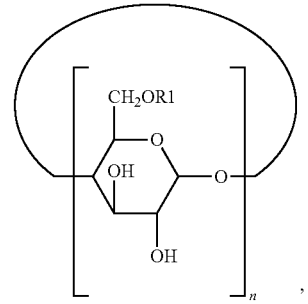

wherein: each R1 is independently selected from the group consisting of a hydrophobic group, a sulfite, and H; and n is 6, 7, or 8. In some cases, the hydrophobic group is selected from alkyl (e.g., $C_1$-$C_6$ or $C_2$-$C_6$ alkyl), alkenyl (e.g., $C_1$-$C_6$ or $C_2$-$C_6$ alkenyl), alkynyl (e.g., $C_1$-$C_6$ or $C_2$-$C_6$ alkynyl), haloalkyl (e.g., $C_1$-$C_6$ or $C_2$-$C_6$haloalkyl), cycloalkyl (e.g., $C_1$-$C_6$ or $C_2$-$C_6$cycloalkyl), aryl (e.g., $C_6$ aryl), and any combination thereof. In some cases, the hydrophobic group is selected from hydroxyalkyl (e.g., $C_1$-$C_6$ or $C_2$-$C_6$ alkyl), alkyl (e.g., $C_1$-$C_6$ or $C_2$-$C_6$ alkyl), alkenyl (e.g., $C_1$-$C_6$ or $C_2$-$C_6$ alkenyl), alkynyl (e.g., $C_1$-$C_6$ or $C_2$-$C_6$ alkynyl), haloalkyl (e.g., $C_1$-$C_6$ or $C_2$-$C_6$ haloalkyl), cycloalkyl (e.g., $C_1$-$C_6$ or $C_2$-$C_6$ cycloalkyl), aryl (e.g., $C_6$ aryl), and any combination thereof. In some cases, the sulfite is a ($C_1$-$C_6$-alkyl or alkylene)-$SO_3^-$ group or a ($C_2$-$C_6$-alkyl or alkylene)-$SO_3^-$ group.

In some cases, the emulsion (e.g., the aqueous phase of the emulsion) contains a cyclodextrin that is a compound of Formula I or contains a mixture of cyclodextrins compounds of Formula I, wherein n is 6. In some cases, the emulsion (e.g., the aqueous phase of the emulsion) contains a cyclodextrin that is a compound of Formula I or contains a mixture of cyclodextrins compounds of Formula I, wherein n is 7. In some cases, the emulsion (e.g., the aqueous phase of the emulsion) contains a cyclodextrin that is a compound of Formula I or contains a mixture of cyclodextrins compounds of Formula I, wherein n is 8.

In some cases, the emulsion comprises a mixture of at least two structurally different cyclodextrin molecules (e.g., 2 to 5, 2 to 20, or 2 to 30) of Formula I, wherein n is 6. In some cases, the emulsion comprises a mixture of at least two structurally different cyclodextrin molecules (e.g., 2 to 5, 2 to 20, or 2 to 30) of Formula I, wherein n is 7. In some cases, the emulsion comprises a mixture of at least two structurally different cyclodextrin molecules (e.g., 2 to 5, 2 to 20, or 2 to 30) of Formula I, wherein n is 8.

In some cases, each R1 is independently H or an hydroxyalkyl, wherein at least one R1 is hydroxyalkyl. In some cases, each R1 is independently H or a $C_2$-$C_6$ hydroxyalkyl, wherein at least one R1 is $C_2$-$C_6$ hydroxyalkyl. In some cases, each R1 is independently H or a $C_2$-$C_6$ hydroxyalkyl, wherein at least one R1 is 2-hydroxypropyl. In some cases, at least two R1 are 2-hydroxypropyl. In some cases, at least three, at least four, or at least five R1 are 2-hydroxypropyl. In some cases, n is 7 or 8 and at least 6 R1 are 2-hydroxypropyl. In some cases, n is 8 and at least 7 R1 are 2-hydroxypropyl. In some cases, each R1 is 2-hydroxypropyl.

In some cases, the cyclodextrin component in the W/O emulsion droplets is or comprises 2-hydroxypropyl α-cyclodextrin. In some cases, the cyclodextrin component in the W/O emulsion droplets is or comprises 2-hydroxypropyl β-cyclodextrin. In some cases, the cyclodextrin component in the W/O emulsion droplets is or comprises 2-hydroxypropyl γ-cyclodextrin.

Additional cyclodextrins include but are not limited to those described in U.S. 2015/0025023; U.S. 2009/0012042; WO 2015/042759; U.S. Pat. Nos. 5,241,059; 5,173,481, and mixtures thereof.

B. Polymers

Water-in-oil (W/O) emulsion droplets described herein also contain a linear or branched, substituted or unsubstituted, polymer or a mixture of different polymers capable forming a host-guest complex with the cyclodextrin in the droplets. In some embodiments, the polymer is a linear polymer. In some cases, the polymer is a branched polymer, such as a dendrimer, or a star shaped polymer. In some cases, the polymer has a number average molecular weight or weight average molecular weight of about 2,000, from about 2,000 to about 70,000, or from about 7,000 to about 10,000. In some cases, the polymer has a number average molecular weight or weight average molecular weight of from about 10 kDa to about 40 kDa, from about 15 kDa to about 40 kDa, from about 10 kDa to about 70 kDa, or from about 150 kDa to about 260 kDa.

In some cases, the polymer is a hydrophobic polymer (e.g., hydrophobic as compared to a linear poly(ethylene glycol) (CAS 25322-68-3) having an average molecular weight of 8000 (e.g., Sigma-Aldrich Product No. P5413)). In some cases, the polymer is a hydrophilic polymer, such as a poly(ethylene glycol) (PEG) polymer. In some cases, the polymer is a linear or branched PEG polymer. In some cases, the polymer is a PEG polymer, such as a PEG described in *Macromolecules* 1990, 23, 2821; Macromolecules 1993, 26, 5698; Carbohydr. Res. 1998, 305, 127; or Advanced Drug Delivery Reviews 60 (2008) 1000-1017.

In an exemplary embodiment, the PEG polymer is a star-poly(ethylene glycol) (sPEG). For example, the PEG polymer can be an sPEG as described in Langmuir 2003, 19, 9680-9683. As another example, the PEG polymer can be an sPEG having 3, 4, 5, 6, 7, 8, 9, 10, 11, 12, 13, 14, 15, 16, 17, 18, 19, 20, 21, 22, 23, or 24, or more arms. As another example, the PEG polymer can be an sPEG having from 4 to 24, from 10 to 24, from 4 to 20, from 10 to 20, from 4 to 15, or from 10 to 15 arms. In some cases, the sPEG has a number average molecular weight or weight average molecular weight of about 2,000, from about 2,000 to about 70,000, or from about 7,000 to about 10,000. In some cases, the sPEG has a number average or weight average molecular weight of from about 10 kDa to about 40 kDa, from about 15 kDa to about 40 kDa, from about 10 kDa to about 70 kDa, or from about 150 kDa to about 260 kDa. Exemplary sPEG polymers useful in the present invention include, but are not limited to those available from NEKTAR (see, 3-arm, 4-arm, and 8-arm sPEGs available from www.sejinbio.co.kr/Catalogue/Nektar), and/or those described in Macromolecules, 2002, 35 (5), pp 1980-1983; or Macromolecules, 2008, 41, 1766-1773.

In some cases, the polymer is a polycaprolactone polymer, such as a polycaprolactone described in Macromolecules, 2000, 33, 4472-4477; or Macromolecules, 2003, 36, 2742-2747. In some cases, the polymer is a poly(propylene glycol) polymer, such as a poly(propylene glycol) polymer described in J. Chem. Soc., Chem. Commun., 1990, 1322; or M. Macromolecules, 1995, 28, 8406. In some cases, the polymer is a poly(methyl vinyl ether) polymer, such as a poly(methyl vinyl ether) polymer described in Chem. Lett. 1993, 237; or Bull. Chem. Soc. Jpn., 1998, 71, 535. In some cases, the polymer is an oligoethylene polymer, such as an oligoethylene polymer described in Bull. Chem. Soc. Jpn. 1994, 67, 2808.

In some cases, the polymer is a polyisobutylene polymer, such as a polyisobutylene polymer described in Macromolecules, 1993, 26, 5267; or Macromolecules, 1996, 29, 5611. In some cases, the polymer is a polylacticacid polymer, such as a polylacticacid polymer described in Macromolecules, 2003, 36, 2742-2747. In some cases, the polymer is a poly(hydroxybutyrate) polymer, such as a poly(hydroxybutyrate) polymer described in Macromolecules, 2002, 35 (8), pp 3126-3132; Macromolecules, 2002, 35 (9), pp 3778-3780; or Biomacromolecules, 2003 November-December; 4(6):1865-7. In some cases, the polymer is a poly(tetrahydrofuran) polymer, such as a poly(tetrahydrofuran) polymer described in Macromolecules, 1999, 32 (21), pp 7202-7207; J. Phys. Chem. B, 2003, 107 (1), pp 14-19; or Polymer, Volume 45, Issue 6, March 2004, Pages 1777-1785. In some cases, the polymer is a polymer of cholesterol or a derivative thereof, such as those described in Biomacromolecules, 2014 Jun. 9; 15(6):2206-17; or Macromol. Chem. Phys., 2014 215: 163-170. As described herein, the foregoing polymers can be homopolymers or co-block polymers. In some cases, one or more of the monomer components of the foregoing polymers are suitable as a monomer or polymer block of a block co-polymer, e.g., as further described below.

In some cases, the polymer is an amphiphilic polymer having a hydrophobic portion and a hydrophilic portion. The amphiphilic polymers can be non-ionic amphiphilic polymers (e.g., non-ionic amphiphilic copolymers). In some cases, the polymer is a block co-polymer (e.g., a di-block, tri-block, tetra-block, or penta-block co-polymer). In some cases, the amphiphilic polymer is a block co-polymer (e.g., a di-block, tri-block, tetra-block, or penta-block co-polymer). Amphiphilic block co-polymers typically have at least one hydrophilic block and at least one hydrophobic block. Exemplary hydrophilic blocks include, but are not limited to ethylene glycol, caprolactone, lactic acid, and the like. Exemplary hydrophobic blocks include propylene glycol, hydroxybutyrate, tetrahydrofuran, isobutylene, ethylene, methyl vinyl ether, cholesterol, a cholesterol derivative, and the like.

In some cases, hydrophilic and/or hydrophobic blocks of a co-polymer are monomer blocks. An exemplary monomer containing amphiphilic block co-polymer is [ethyleneglycol-propyleneglycol]$_n$, where n is an integer (e.g., from 2 to 10,000). Alternatively, hydrophilic and/or hydrophobic blocks of a co-polymer are polymer blocks. Exemplary polymer block containing amphiphilic block co-polymer include [ethyleneglycol]$_x$-[propyleneglycol]$_y$, where x and y are integers, and can be the same or different (i.e., polyethyleneglycol-polypropyleneglycol). Another exemplary polymer block containing amphiphilic block co-polymer is [ethyleneglycol]$_x$-[propyleneglycol]$_y$-[ethyleneglycol]$_z$, where x and y are integers, and can be the same or different (i.e., polyethyleneglycol-polypropyleneglycol-polyethyleneglycol).

In some cases, the amphiphilic block co-polymers are tri-block co-polymers, such as poloxamers. Poloxamers are (A-B-A) tri-block co-polymers that contain a polyoxypropylene core block (B) flanked on both sides by a polyoxyethylene block (A). Poloxamers are commonly referred to by a three digit numbering system. The first two digits x 100 give the approximate molecular mass of the polyoxypropylene core, and the last digit x 10 gives the percentage polyoxyethylene content. In some embodiments the poloxamer is a poloxamer or mixture of poloxamers described by the general formula:

wherein a' and a can be the same or different and each is an integer such that the hydrophilic portion represented by (C$_2$H$_4$O) constitutes approximately 60% to 90% by weight of the copolymer, such as such as 70% to 90%, by weight, of the copolymer; and b is an integer such that the hydrophobe represented by (C$_3$H$_6$O)6 (i.e. the polyoxypropylene portion of the copolymer) has a molecular weight of approximately 950 to 4000 daltons (Da), such as about 1,200 to 3,500 Da, for example, 1,200 to 2,300 Da, 1,500 to 2,100 Da, 1,400 to 2,000 Da or 1,700 to 1,900 Da. For example, the molecular weight of the hydrophilic portion can be between 5,000 and 15,000 Da. Exemplary poloxamers having the general formula described above include poloxamers wherein a or a' is an integer 5-150 and b is an integer 15-75, such as poloxamers wherein a is an integer 70-105 and b is an integer 15-75. Exemplary poloxamers include, but are not limited to poloxamer 188, poloxamer 184, poloxamer 182, poloxamer 181, poloxamer 124, poloxamer 407, poloxamer 331, and poloxamer 338.

In some embodiments, the polymer component of the cyclodextrin:polymer host guest complex is a mixture of two or more of the foregoing polymers or mixtures thereof.

The cyclodextrin and/or polymer can be selected to form a rotaxane. As used herein, the term "rotaxane" refers to a cyclodextrin and polymer complex in which the polymer is threaded through the central core of the cyclodextrin and kinetically trapped from dissociation by the presence of a bulky head group at polymer ends on each side of the threaded cyclodextrin molecule. The cyclodextrin and/or polymer can be selected to form a pseudorotaxane. As used herein, the term "pseudorotaxane" refers to a cyclodextrin and polymer complex in which the polymer is threaded through the central core of the cyclodextrin and relatively kinetically free to dissociate due to the absence of bulky head group at polymer ends on each side of the threaded cyclodextrin molecule. The pseudorotaxane complexes can be stabilized by hydrophobic non-covalent interactions between the cyclodextrin and the polymer. Moreover, pseudorotaxane complexes can be more temperature sensitive than rotaxane complexes due to the absence of the stabilizing bulky head groups. In some cases, the temperature dependence of the hydrophobic effect or other non-covalent interaction can be utilized to form pseudortoaxane complexes that form at relatively high temperatures, and dissociate at relatively low temperatures. In some embodiments, this effect can provide a thermally reversible hydrogel having a sol form at a low temperature and a gel form at a high temperature as described herein.

The cyclodextrin and/or polymer can be selected to form a polyrotaxane. As used herein, the term "polyrotaxane" refers to a cyclodextrin and polymer complex in which a polymer molecule is threaded through the central core of multiple cyclodextrin molecules and kinetically hindered from dissociation by the presence of the bulky head groups at polymer ends. The cyclodextrin and/or polymer can be selected to form a polypseudorotaxane. As used herein, the term "pseudorotaxane" refers to a cyclodextrin and polymer complex in which the polymer is threaded through the central core of multiple cyclodextrin molecules and relatively kinetically free to dissociate due to the absence of bulky head group at polymer ends on each side of the threaded cyclodextrin molecules. The polypseudorotaxane complexes can be stabilized by hydrophobic non-covalent interactions between the cyclodextrin and the polymer. Moreover, polypseudorotaxane complexes can be more temperature sensitive than polyrotaxane complexes due to the absence of the stabilizing bulky head groups. In some cases, the temperature dependence of the hydrophobic effect or other non-covalent interaction can be utilized to form polypseudorotaxane complexes that form at relatively high temperatures, and dissociate at relatively low temperatures. In some embodiments, this effect can provide a thermally reversible hydrogel having a sol form at a low temperature and a gel form at a high temperature as described herein.

C. Oil Phase

The W/O emulsion droplets are present in a continuous oil phase. Typically, the continuous oil phase contains a fluorous oil, a silicon oil, or a combination thereof. Non-limiting examples of fluorous oils suitable for use as a continuous oil phase or in a continuous oil phase include methyl nonafluorobutyl ether (HFE-7100), ethyl nonafluorobutyl ether (HFE-7200), 2-trifluoromethyl-3-ethoxydodeca-fluorohexane (HFE-7500), 1,1,1,2,2,3,4,5,5,5-decafluoro-3-methoxy-4-trifluoromethyl-pentane (HFE-7300), perfluorooctylbromide, perfluorodecalin, FC-40, FC-43, FC-70, FC-770, FC-84, FC-72, RM-82, FC-75, RM-101, or a combination thereof.

The continuous oil phase can also contain a surfactant, such as a fluorosurfactant. In some cases, the fluorosurfactant is perfluorinated or is a block co-polymer that contains a perfluorinated block. Exemplary fluorosurfactants suitable for use in a continuous oil phase include, but are not limited to, Krytox fluorosurfactants such as Krytox FSH (Krytox FSH 157), fluorosurfactants described in U.S. Pat. No. 9,012,390, and mixtures thereof. The surfactant in the continuous oil phase can be present at a concentration of from about 0.01% to about 5%, from about 0.1% to about 4%, from about 0.5% to about 3%, from about 1% to about 3%, or about 2% (w/w). In some embodiments, the oil phase comprises an ionic fluorosurfactant. In some embodiments, the ionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

III. Methods

Described herein are methods of making one or more of the foregoing W/O emulsion droplet compositions. Typically, the method includes combining three or more aqueous phase components (e.g., water, cyclodextrin, and polymer) to form an aqueous reaction mixture and then combining the aqueous reaction mixture with one or more oil phase components (e.g., fluorous and/or silicone oil and optionally fluorosurfactant) to form an emulsion pre-mixture. The pre-mixture can be emulsified using methods known in the art to form a plurality of W/O emulsion droplets. For example, the emulsion pre-mixture can be sonicated, vortexed, blended, or a combination thereof to form the W/O emulsion droplets. Alternatively, the aqueous reaction mixture and oil phase components can be combined using methods to directly generate a plurality of W/O emulsion droplets without an intervening emulsion pre-mixture. For example, a microfluidic device can be used to generate emulsion droplets in a continuous oil phase by injecting a plurality of droplet-size volumes of aqueous reaction mixture into the continuous oil phase.

As yet another alternative, W/O emulsion droplets can be generated by combining a continuous oil phase (e.g., a base oil and optionally a fluorosurfactant), an aqueous solution (e.g., water or buffered water), a plurality of cyclodextrin molecules, and a plurality of (e.g., amphiphilic) polymer molecules, under conditions wherein at least a portion of the cyclodextrin molecules and the polymer molecules form a plurality of host-guest complexes (e.g., rotaxane, pseudorotaxane, polyrotaxane, or polypseudorotaxane complexes), thereby forming an emulsion comprising a water-in-oil emulsion droplet. As described above, the combining to form the emulsion can be performed in bulk (e.g., with sonicating, vortexing, blending, or a combination thereof) or by injecting a plurality of droplet-size volumes of aqueous reaction mixture into the continuous oil phase. In some cases one or more components of the aqueous phase, one or more components of the continuous phase, or a combination thereof, are not included in the emulsification, but added at a later time, e.g., by injection of the component into the droplet, or by merging droplets. Methods, compositions, devices, and systems for injecting or merging components into a droplet or a plurality of droplets include but are not limited to those described in U.S. 2015/0209785; U.S. 2016/0131675; U.S. 2015/0321163; U.S. 2013/0344485; U.S. 2015/0024945; U.S. 2015/0045258; U.S. 2015/0065396; U.S. 2016/0001289; and U.S. 2016/0045914, each of which are incorporated by reference in the entirety for any and all purposes including but not limited to droplet compositions, droplet methods, and devices and systems for making and/or using droplets for analysis of biological analytes such as nucleic acids.

Also described herein are methods of using a W/O emulsion containing a W/O emulsion droplet (e.g., a plurality of W/O emulsion droplets). In some embodiments, the emulsion droplets are used in a microfluidic device. Additionally or alternatively, the droplets can be used in a device configured to perform bulk analysis. For example, a plurality of W/O emulsion droplets can be introduced into a PCR tube (e.g., a 0.2 mL PCR tube) and thermocycled in a thermocycler to, e.g., amplify and/or detect nucleic acids. In some embodiments, the emulsion droplets can then be analyzed in a microfluidic device. Alternatively, the emulsion droplets can be thermocycled and analyzed, or generated, thermocycled, and analyzed in a microfluidic device.

In one embodiment, described herein is a method of using a W/O emulsion droplet by providing the emulsion containing the W/O emulsion droplet; heating the droplet to a temperature of between about 50° C. to about 100° C.; cooling the droplet to a temperature below about 50° C.; and optionally repeating the heating and cooling between 1-500, 1-250, 1-100, 1-50, 1-40, 10-500, 10-250, 10-100, 10-40, 20-500, 20-250, 20-100, 20-50, or 20-40 times. In some cases, the method includes heating to a nucleic acid denaturation temperature (e.g., about 95° C., 98° C., or 99° C.), cooling to a nucleic acid primer hybridization and/or polymerization temperature (e.g., about 50° C., 60° C., 65° C., 68° C., 70° C., or 72° C.), optionally heating to a nucleic acid primer polymerization temperature; and optionally repeating the denaturation, hybridization/polymerization, and optional polymerization temperatures between 1-500, 1-250, 1-100, 1-50, 1-40, 10-500, 10-250, 10-100, 10-40, 20-500, 20-250, 20-100, 20-50, or 20-40 times.

In some embodiments at least 100 or at least 1,000, or more W/O emulsion droplets are thermocycled, e.g., as described herein. In some embodiments, after the cooling or repeated heating and cooling of the W/O emulsion droplets, the method further includes injecting at least a portion of the droplet interiors into a plurality of second droplets (e.g., second droplets containing detection reagents).

Citation or identification of any document in this application is not an admission that such document is available as prior art to the present invention. Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

Droplet Stabilization with Poloxamer:Cyclodextrin Emulsions

The poloxamer Pluronic F-68 was tested with α-cyclodextrin at various mixing ratios to identify compositions which formed suitable thermally-reversible host-guest complexes (see, e.g., FIG. 1) and/or, e.g., thermally reversible, supramolecular hydrogels. In this experiment, the Pluronic F-68 and α-cyclodextrin were added to a buffered aqueous PCR master mix comprising KRAS amplicon, DNA polymerase, primers and dNTPs at (8% m/v+2% m/v) and (1% m/v+1% m/v) final concentration, respectively. The droplets containing the PCR master mix were generated by a microfluidic flow-focusing device with an 85 μm nozzle. The oil phase comprised HFE7500 with 2% w/w Krytox-Jeffamine-Krytox based triblock copolymer as fluoro-phase surfactant. Upon generation, droplets-oil mixtures comprising 70-90 μL droplets and 30-10 μL oil were transferred to 200 μL PCR tubes at a total volume of 100 μL per tube then thermal cycled on Bio-Rad MyCycler™ thermal cycler.

Figure 2:
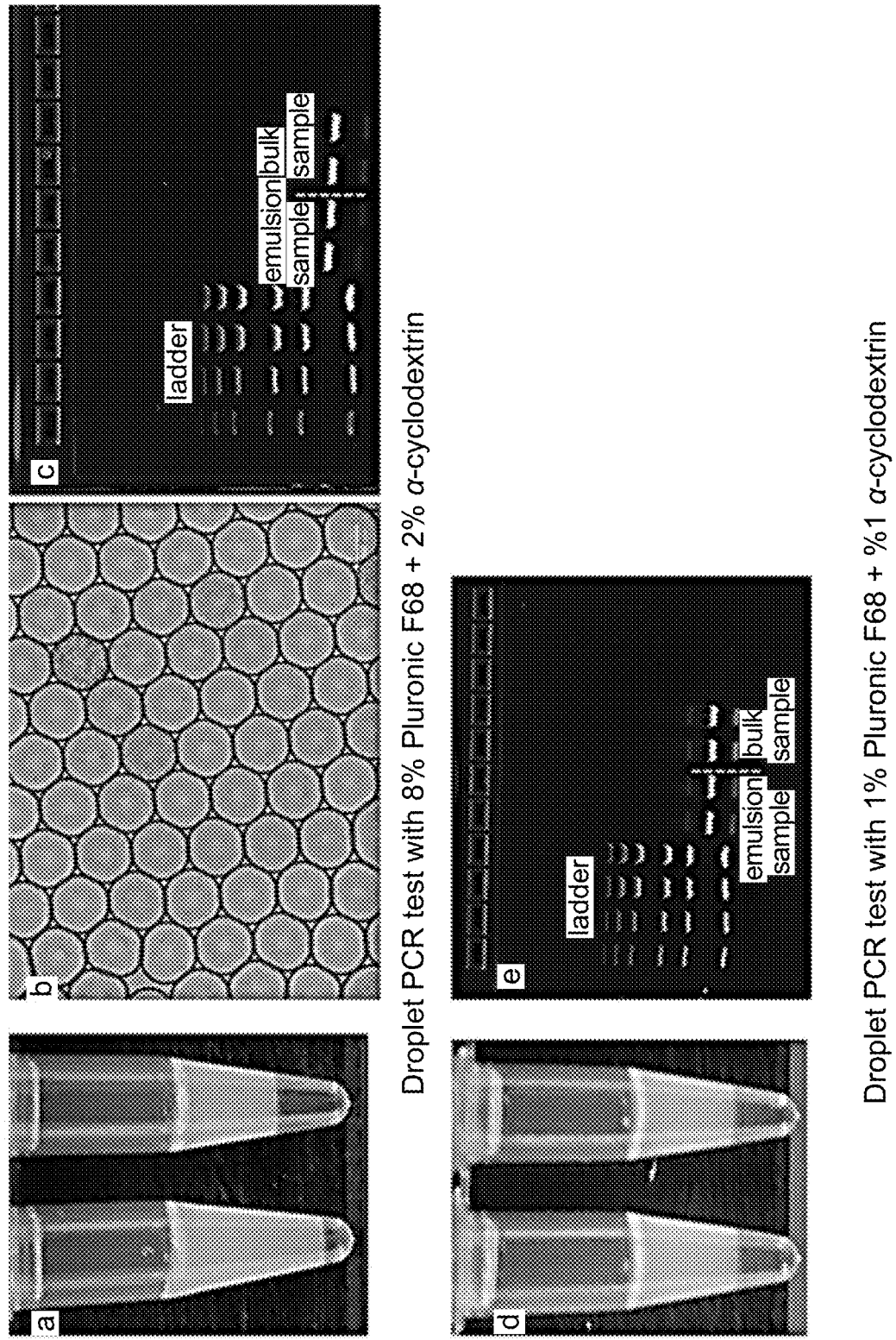
FIG. 2 shows the droplets stabilization capability and PCR compatibility of supramolecular hydrogel formed with Pluronic F-68 and α-cyclodextrin at different mixing ratios.

After thermal cycling, the droplets were visually inspected in bulk (FIG. 2a, 2d) and on Bio-Rad ZOE™ Fluorescent Cell Imager (FIG. 2b) to capture any coalescence instance. FIG. 2a, 2b, 2d demonstrated that the droplets stabilized with supramolecular hydrogel were highly monodispersed with minimum coalescence post thermal cycling.

The droplets were broken by mixing with 1H,1H,2H,2H-Perfluoro-1-octanol at 1:1 volume ratio for gel electrophoresis analysis. The gel electrophoresis demonstrated that the supramolecular hydrogel additive is compatible with PCR (FIG. 2c, 2e).

Figure 3:
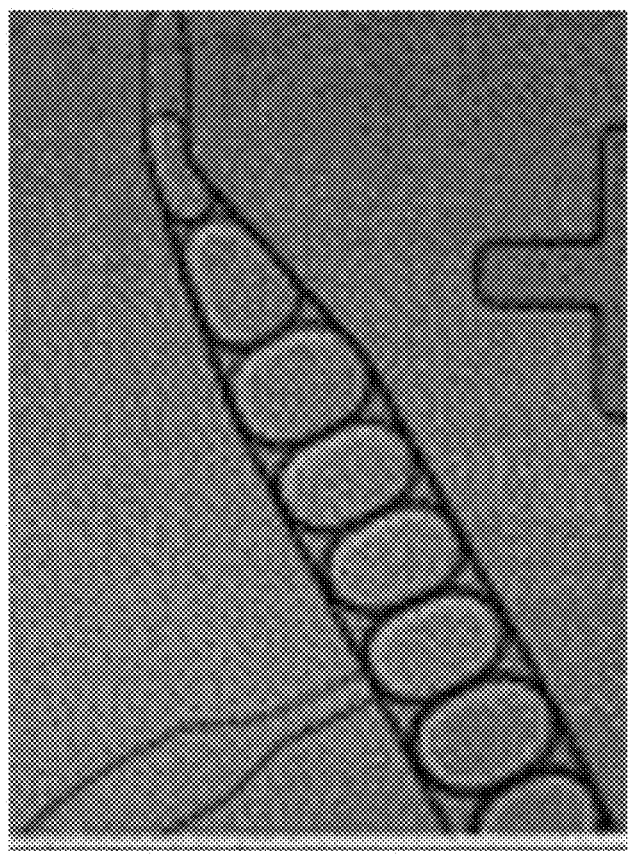
FIG. 3 demonstrates the droplets stabilization capability of supramolecular hydrogel on Bio-Rad MonoRAyL hotspot sequencing system.
Figure 4:
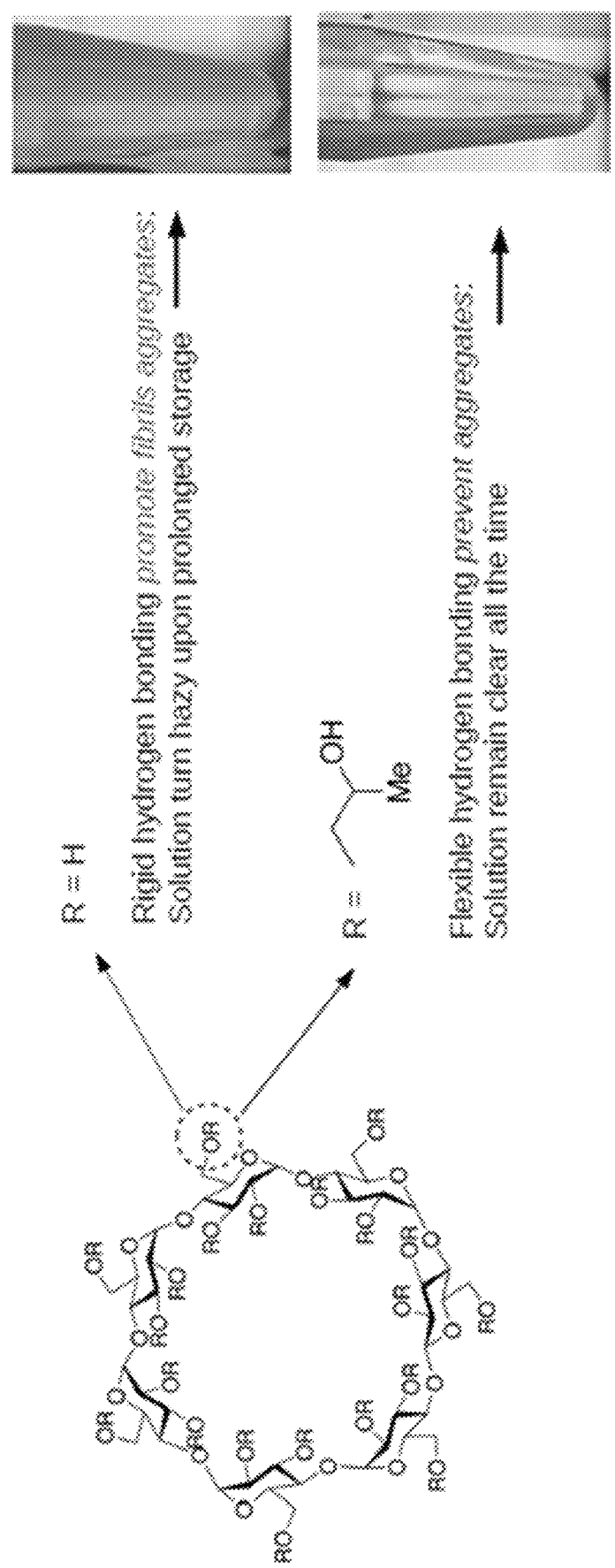
FIG. 4 demonstrates the impact of cyclodextrin structure on supramolecular hydrogel sample turbidity.

Droplets Stabilization Capability of Supramolecular Hydrogel on Bio-Rad Monorayl Hot-Spot Sequencing System In this experiment, the Pluronic F-68 and 2-hydroxypropyl-α-cyclodextrin were added to a buffered aqueous PCR master mix comprising KRAS amplicon, DNA polymerase, primers and dNTPs at 2% m/v+2% m/v final concentration. The droplets containing the PCR master mix were generated and thermal cycled with Bio-Rad MonoRAyL hot-spot sequencing system. FIG. 3 shows highly monodispersed droplets post on-chip thermal cycling.

Supramolecular Hydrogel Sample Turbidity Dependence on Cyclodextrin Molecular Structure In this experiment, aqueous PCR master mix were prepared with 2% Pluronic F-68+2% α-cyclodextrin and 2% Pluronic F-68+2% 2-hydroxypropyl-α-cyclodextrin, respectively and the mastermix solutions were stored at 4° C. for two weeks. The sample prepared from α-cyclodextrin (top image) showed increased turbidity upon prolonged storage while the sample prepared from 2-hydroxypropyl-α-cyclodextrin (bottom image) still remained clear.

Figure 5:
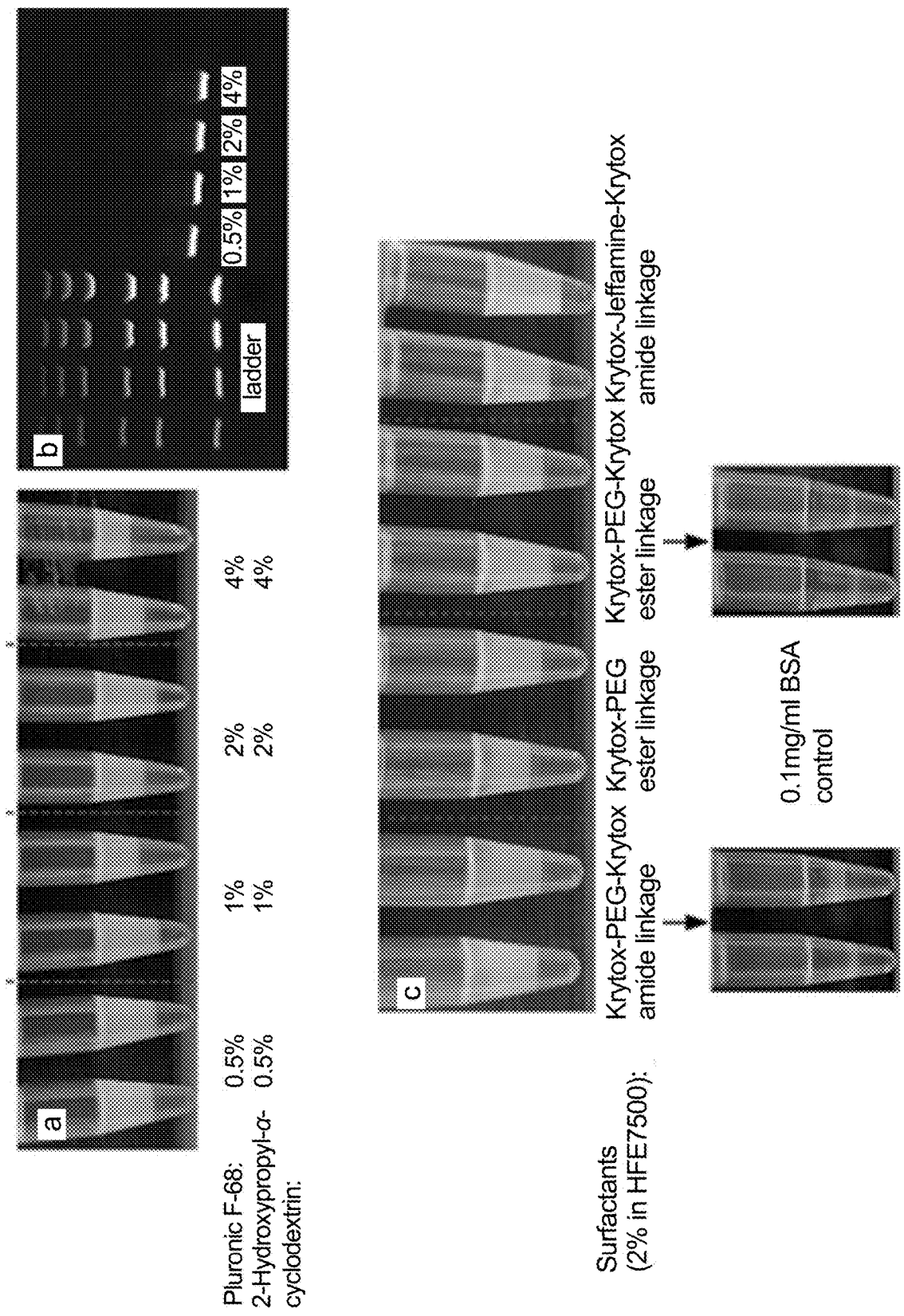
FIG. 5A-C illustrates results of testing water-in-oil emulsion droplet chemistries described herein having various host (cyclodextrin) and guest (polymer) concentrations and different oil compositions as indicated.

Droplets Stabilization Capability and PCR Compatibility of Supramolecular Hydrogel Formed with Pluronic F-68 and 2-Hydroxypropyl-A-Cyclodextrin at Different Concentrations and with Different Oil-Phase Surfactants In this experiment, the Pluronic F-68 and 2-hydroxypropyl-α-cyclodextrin were added to a buffered aqueous PCR master mix comprising KRAS amplicon, DNA polymerase, primers and dNTPs at (0.5% m/v+0.5% m/v), (1% m/v+1% m/v), (2% m/v+2% m/v) and (4% m/v+4% m/v) final concentration, respectively. The droplets containing the PCR master mix were generated by a microfluidic flow-focusing device with 85 μm nozzle. The oil phase comprised HFE7500 with 2% w/w Krytox-PEG based diblock copolymer as fluoro-phase surfactant. Upon generation, droplets-oil mixtures comprising 70-90 μL droplets and 30-10 μL oil were transferred to 200 μL PCR tubes at a total volume of 100 μL per tube then thermal cycled on Bio-Rad MyCycler™ thermal cycler. After PCR, the emulsions were visually inspected in bulk. FIG. 5a shows that emulsions prepared with different concentration of supramolecular hydrogel retained good stability post thermal cycling. The droplets were broken by mixing with 1H, 1H,2H,2H-Perfluoro-1-octanol at 1:1 volume ratio for gel electrophoresis analysis. The gel electrophoresis demonstrated that the supramolecular hydrogel additive is compatible with PCR at the tested concentration range (FIG. 5b).

Similarly, Pluronic F-68 and 2-hydroxypropyl-α-cyclodextrin were added to a buffered aqueous PCR master mix comprising KRAS amplicon, DNA polymerase, primers and dNTPs at 2% m/v+2% m/v final concentration. The droplets containing the PCR master mix were generated by a microfluidic flow-focusing device with 85 μm nozzle. The oil phase comprised HFE7500 with 2% w/w of different types of fluoro-phase surfactant: 1. Krytox-PEG-Krytox based triblock copolymer with amide linkage; 2. Krytox-PEG based diblock copolymer with ester linkage; 3. Krytox-PEG-Krytox based triblock copolymer with ester linkage; and 4. Krytox-Jeffamine-Krytox based triblock copolymer with amide linkage. Upon generation, droplets-oil mixtures comprising 70-90 μL droplets and 30-10 μL oil were transferred to 200 μL PCR tubes at a total volume of 100 μL per tube then thermal cycled on Bio-Rad MyCycler™ thermal cycler. After PCR, the emulsions were visually inspected in bulk. FIG. 5c shows that emulsions prepared with supramolecular hydrogel exhibit good thermal stability with different types of fluoro-phase surfactant. The droplets without supramolecular hydrogel were prepared as negative control and they showed severe coalescence post thermal cycling.

Figure 6:
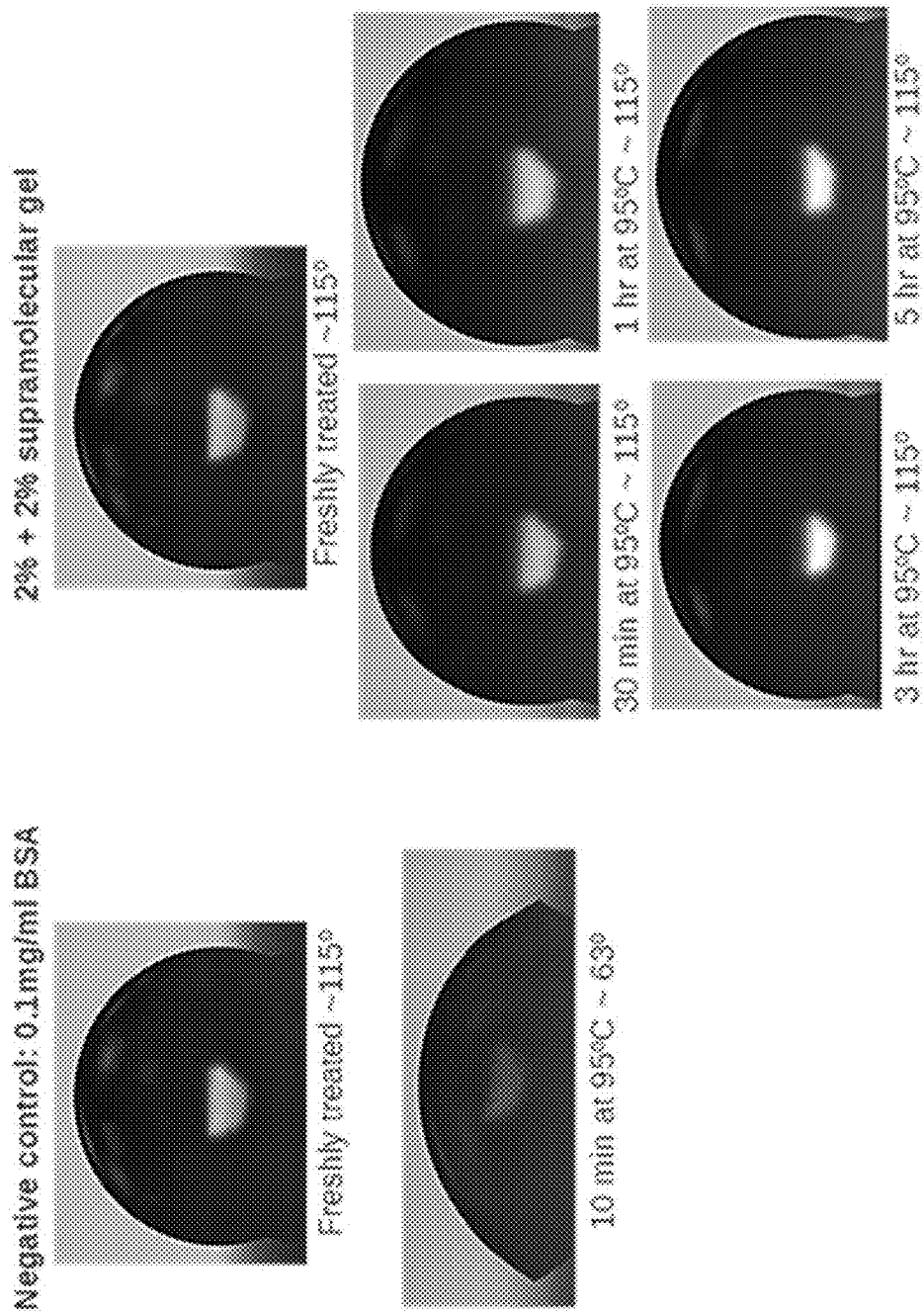
FIG. 6 demonstrates low adhesion of PCR master mix prepared from supramolecular hydrogel to the COP surface.

Low Adhesion of PCR Master Mix Prepared from Supramolecular Hydrogel to the COP Surface Demonstrates Resistance to Surface Fouling In this experiment, the Pluronic F-68 and 2-hydroxypropyl-α-cyclodextrin were added to a buffered aqueous PCR master mix comprising KRAS amplicon, DNA polymerase, primers and dNTPs at 2% m/v+2% m/v final concentration. The master mix without supramolecular gel but containing 0.1 mg/ml BSA was prepared as negative control. A small plaque of hydrophobically coated COP sample was submerged into master mix and was heated at 95° C. in a sealed vial. The contact angle of the COP plaque was measured to capture any sample adhesion to the surface. FIG. 6 shows that the contact angle of COP maintained same over 5 hours incubation at 95° C. in the supramolecular hydrogel master mix, indicating minimum sample adhesion to the surface. In contrast, the COP plaque exposed to 0.1 mg/ml BSA master mix shows rapid decrease in contact angle, indicating significant sample adhesion to the surface.

What is claimed is:

1. An emulsion comprising a water-in-oil emulsion droplets, the droplets comprising:
   water;
   a plurality of cyclodextrin molecules, wherein at least some of the cyclodextrin molecules comprise 2-hydroxypropyl α-cyclodextrin, 2-hydroxypropyl β-cyclodextrin, or 2-hydroxypropyl γ-cyclodextrin; and
   a plurality of amphiphilic polymer molecules, wherein individual amphiphilic polymer molecules of the plurality comprise a hydrophobic moiety and a hydrophilic moiety, wherein the amphiphilic polymer molecules are poloxamers;
   wherein at least a portion of the cyclodextrin molecules and the amphiphilic polymer molecules form a thermally-reversible hydrogel that is in sol form at at least one temperature between 0-70° C., wherein the thermally-reversible hydrogel comprises a plurality of polypseudorotaxane complexes, and
   wherein the droplets are present in a continuous oil phase.

2. The emulsion of claim 1, wherein a mass ratio of cyclodextrin molecules to amphiphilic polymer molecules in the droplets is from about 1:4 to about 4:1.

3. The emulsion of claim 1, wherein a mass ratio of cyclodextrin molecules to amphiphilic polymer molecules in the droplets is 1:1.

4. The emulsion of claim 1, wherein the concentration of cyclodextrin molecules in the droplets is from 0.5% to 4% mass per volume (m/v).

5. The emulsion of claim 4, wherein the concentration of cyclodextrin molecules is 2% mass per volume (m/v).

6. The emulsion of claim 4, wherein the poloxamers are poloxamer 188.

7. The emulsion of claim 1, wherein the cyclodextrin molecules comprise 2-hydroxypropyl α-cyclodextrin.

8. The emulsion of claim 1, wherein the cyclodextrin molecules comprise 2-hydroxypropyl β-cyclodextrin.

9. The emulsion of claim 1, wherein the cyclodextrin molecules comprise 2-hydroxypropyl γ-cyclodextrin.

10. The emulsion of claim 1, wherein the poloxamers are poloxamer 188.

11. The emulsion of claim 1, wherein the droplets further comprise a thermostable DNA-dependent DNA polymerase or an RNA-dependent DNA polymerase.

12. The emulsion of claim 1, wherein the droplets further comprise nucleic acid.

13. The emulsion of claim 1, wherein the droplets comprise a thermally reversible hydrogel.

14. The emulsion of claim 1, wherein the droplets are present in a continuous fluorocarbon oil phase.

15. The emulsion of claim 14, wherein the continuous fluorocarbon oil phase comprises a fluorous oil and a surfactant.

16. The emulsion of claim 15, wherein the surfactant is a fluorosurfactant.

17. The emulsion of claim 16, wherein the fluorosurfactant is a block co-polymer comprising a perfluorinated polyether block and a polyethylene glycol block.

18. A method of forming an emulsion according to claim 1, the method comprising:
   combining a continuous oil phase, an aqueous solution, a plurality of cyclodextrin molecules, and a plurality of amphiphilic polymer molecules, under conditions wherein at least a portion of the cyclodextrin molecules and the amphiphilic polymer molecules form a plurality of polypseudorotaxane complexes, thereby forming an emulsion comprising water-in-oil emulsion droplets.

19. A method of using an emulsion comprising water-in-oil emulsion droplets, the method comprising:
   providing the emulsion according to claim 1;
   heating the droplets to a temperature of between about 50° C. to about 100° C.;
   cooling the droplets to a temperature below about 50° C.; and
   optionally repeating the heating and cooling between 1-50 times.

* * * * *